(12) United States Patent
Detinkin

(10) Patent No.: US 10,247,678 B1
(45) Date of Patent: Apr. 2, 2019

(54) ARRANGEMENT AND PROCEDURE FOR THE INSPECTION OF MOVING PLATE-SHAPED OBJECTS

(71) Applicant: BAUMER INSPECTION GMBH, Constance (DE)

(72) Inventor: Igor Detinkin, Constance (DE)

(73) Assignee: BAUMER INSPECTION GMBH, Konstanz (DE)

( * ) Notice: Subject to any disclaimer, the term of this patent is extended or adjusted under 35 U.S.C. 154(b) by 0 days.

(21) Appl. No.: 16/143,476

(22) Filed: Sep. 27, 2018

(30) Foreign Application Priority Data

Sep. 29, 2017 (DE) .......... 10 2017 009 153

(51) Int. Cl.

| | | |
|---|---|---|
| H04N 1/387 | (2006.01) | |
| G03B 37/02 | (2006.01) | |
| G01M 11/00 | (2006.01) | |
| G01N 21/88 | (2006.01) | |
| G01N 21/95 | (2006.01) | |
| G01N 21/89 | (2006.01) | |

(52) U.S. Cl.
CPC ..... *G01N 21/8806* (2013.01); *G01N 21/8851* (2013.01); *G01N 21/8901* (2013.01); *G01N 21/95* (2013.01); *G01N 2021/8835* (2013.01); *G01N 2021/8887* (2013.01)

(58) Field of Classification Search
CPC .... G01N 21/84; G01N 21/95; G01N 21/8806; G01N 21/8851; G01N 21/8901; G01N 2021/8835; G01N 2021/8887; G01N 33/00; G01N 29/04; G01B 11/24; G01B 11/25; B07C 7/00; B07C 3/08; B07C 3/18; B07C 3/14; B07C 3/10; B65G 15/30; B31B 1/00; H04N 5/228; H04N 7/18; H04N 13/02; G06K 9/00
See application file for complete search history.

(56) References Cited

U.S. PATENT DOCUMENTS

| | | | |
|---|---|---|---|
| 2009/0128648 A1* | 5/2009 | Ikeda ............... | G01B 21/04 348/222.1 |
| 2018/0311704 A1* | 11/2018 | Gil ................... | B07C 7/005 |

FOREIGN PATENT DOCUMENTS

| | | |
|---|---|---|
| EP | 0 330 495 A2 | 8/1989 |
| JP | 2016-70865 A | 5/2016 |

* cited by examiner

*Primary Examiner* — Jamil Ahmed
(74) *Attorney, Agent, or Firm* — Norman B. Thot

(57) ABSTRACT

An arrangement for an inspection of plate-shaped objects moving relative to a camera device in a direction of motion through at least two observation areas. The arrangement includes the camera device which includes one single camera which comprises a matrix sensor, and an image processor. In a first detection state, a first observation area running diagonally opposite to the direction of motion is represented on a first image area of the camera device and is recorded as a strip-shaped image. In a second detection state, a second observation area is represented on a second image area of the camera device and is recorded as a strip-shaped image. The image processor merges the strip-shaped images recorded in the first detection state and in the second detection state to form two-dimensional images. All image areas are located on the matrix sensor.

9 Claims, 6 Drawing Sheets

ARRANGEMENT AND PROCEDURE FOR THE INSPECTION OF MOVING PLATE-SHAPED OBJECTS

CROSS REFERENCE TO PRIOR APPLICATIONS

Priority is claimed to German Patent Application No. DE 10 2017 009 153.6, filed Sep. 29, 2017. The entire disclosure of said application is incorporated by reference herein.

FIELD

The present invention relates to an arrangement and to a procedure for the inspection of moving plate-shaped objects.

BACKGROUND

The plate-shaped objects may, for example, be panels for furniture. Such plate-shaped objects are processed during production. A processed surface may then be inspected for defects. One problem is, however, that defects may occur through a further processing during processing in places or on surfaces which were previously processed in another processing step, or which remained unprocessed, or which may already have been inspected. These defects may, for example, occur on surfaces adjacent to surfaces that have already been processed.

EP 0 330 495 A2 describes an inspection system for packages, in particular for detecting and evaluating the quality of packages. In this inspection system, identical packages transported on a conveyor are illuminated by a light source and are detected by at least one camera, whereby the camera is optically aligned perpendicular to a surface of the package in question, and an analysis device is provided which responds to the camera output signals to evaluate the camera recording in terms of compliance with the package specification.

SUMMARY

An aspect of the present invention is to provide a solution whereby an inspection of the plate-shaped objects is also possible in places or on surfaces which were previously processed in another processing step, or which remain unprocessed, or which were previously inspected.

In an embodiment, the present invention provides an arrangement for an inspection of plate-shaped objects moving relative to a camera device in a direction of motion through at least two observation areas. The arrangement includes the camera device comprising one single camera which comprises a matrix sensor, and an image processor. In a first detection state, a first observation area running diagonally opposite to the direction of motion is represented on a first image area of the camera device and is recorded as a strip-shaped image. In a second detection state, a second observation area is represented on a second image area of the camera device and is recorded as a strip-shaped image. The image processor is configured to merge the strip-shaped images recorded in the first detection state and in the second detection state to form two-dimensional images. All image areas are located on the matrix sensor.

BRIEF DESCRIPTION OF THE DRAWINGS

The present invention is described in greater detail below on the basis of embodiments and of the drawings in which.

DETAILED DESCRIPTION

Figure 1:
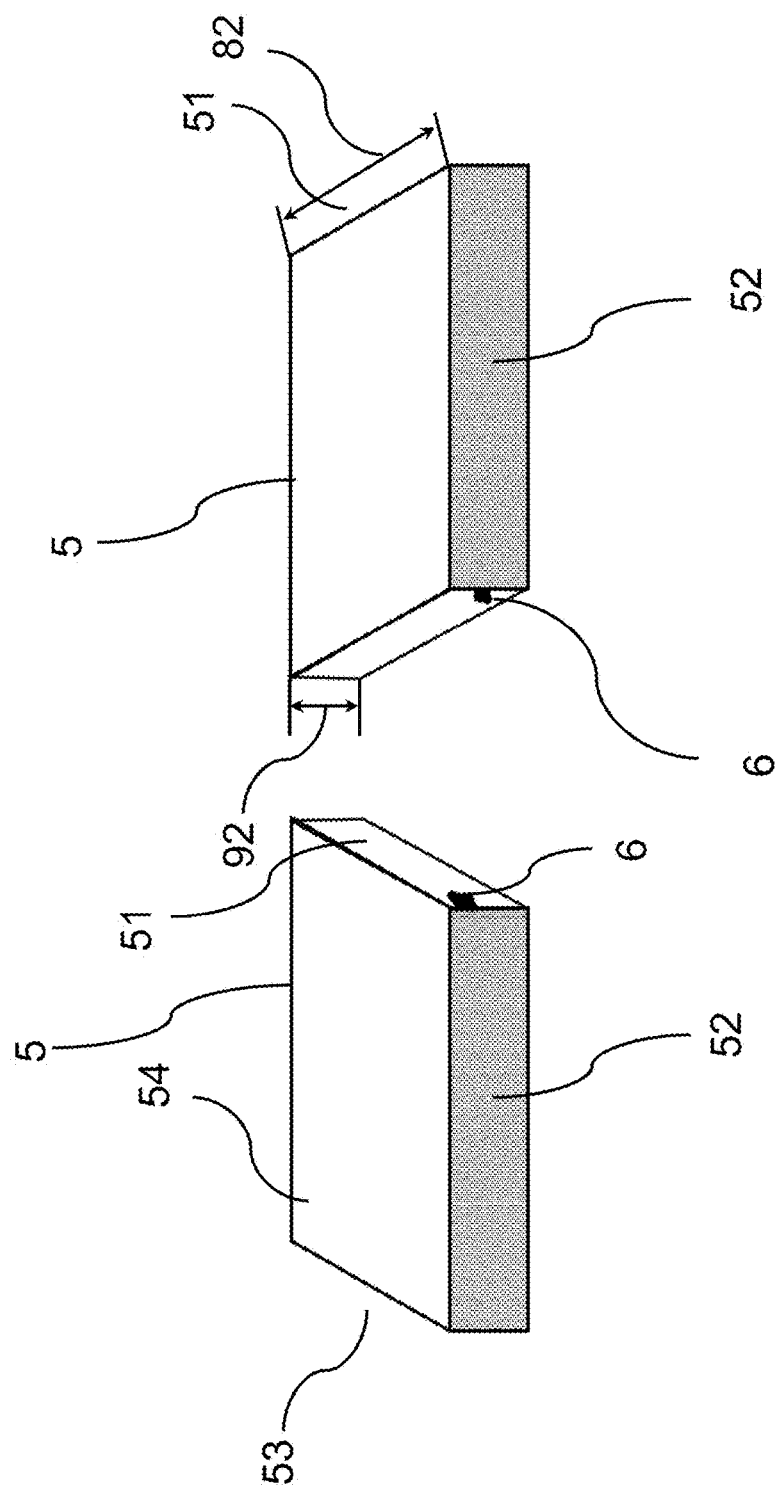
FIG. 1 shows a schematic perspective view of two plate-shaped objects after a processing step.

The present invention provides an arrangement for the inspection of plate-shaped objects moving relative to a camera device in a direction of motion through at least two observation areas, whereby the arrangement comprises the camera device, whereby in one detection state an observation area running diagonally opposite to the direction of motion is represented on an image area of the camera device designed as pixel strips, whereby in a further detection state a further observation area is represented on a further image area of the camera device, and whereby the arrangement also has an image processor which merges the strip-shaped images recorded in the detection states to form two-dimensional images.

The present invention also provides a procedure for the inspection of plate-shaped objects moving relative to a camera device in a direction of motion through observation areas, whereby in one detection state strip-shaped images are recorded along an observation area running diagonally opposite to the direction of motion and whereby in a further detection state strip-shaped images are recorded along a further observation area, and whereby the strip-shaped images recorded in the individual detection states are merged to form a two-dimensional image.

The strip-shaped images comprise or consist of information and image data such as color, brightness, etc., which are detected by suitable elements in the image areas which are designed as pixel strips.

The second image area is designed as pixel strips, whereby the camera device has a single camera with a matrix sensor and all the image areas are located on the matrix sensor.

Such an embodiment may be particularly easy to implement and may take up very little space.

The present invention can be further improved with the following embodiments, each of which is in itself advantageous and which can be combined with each other in any way required, and with the following further developments.

In an embodiment of the present invention, in a first detection state, a first observation area running diagonally opposite to the direction of motion is shown on a first image area of the camera device designed as pixel strips, whereby, in a second detection state, a second observation area is shown on a second image area of the camera device, while in a third detection state, a third observation area running diagonally in the direction of motion is shown on a third image area of the camera device designed as pixel strips, whereby the second observation area is located between the first observation area and the third observation area. The arrangement furthermore has an image processor which merges the strip-shaped images recorded in the detection states to form two-dimensional images.

In the first and third detection states, strip-shaped images are recorded along the first and the third observation area which can then be merged to form a two-dimensional image. This makes it possible to evaluate not only the images of a processed area recorded in the second detection state, as usual, but to also inspect already processed or unprocessed and possibly already inspected areas, in particular adjacent areas.

In an embodiment of the present invention, the first and third image areas of the camera can, for example, each be two-dimensional so that subsequent image processing may be easier than in the case of strip-shaped images.

The second image area can in particular be perpendicular to the direction of motion.

In an embodiment of the present invention, the second image area can, for example, also run diagonally in or opposite to the direction of motion.

The plate-shaped objects may in particular be panels and/or cube-shaped objects.

In an embodiment of the present invention, the camera device can, for example, have one single camera with a matrix sensor, whereby all three image areas are located on the matrix sensor. Image processing can be particularly simple in such an embodiment. The structure can also be particularly simple. A matrix sensor may in particular have a large number of rows and a large number of columns. All images can then be recorded with one single matrix sensor.

The three image areas may advantageously be spaced apart.

In embodiment of the present invention, the three image areas can, for example, overlap each other at least partially. With the help of suitable optical equipment, such as mirrors or the like, the observation areas can, for example, be imaged on one single area in which all three image areas are located. The sensor surface can be kept correspondingly small with such an embodiment.

Images which can be considered to be strip-shaped images are images which have a small width compared to their length, for example, a width that is less than the length by the factor 10. This also applies to pixel strips.

In an embodiment of the present invention, the pixel strips can, for example, have a width of one pixel. This makes the composition of the two-dimensional image particularly simple. A line camera can, for example, be used.

In an embodiment of the present invention, the pixel strips can, for example, have a width of more than one pixel, for example, two to five pixels. In an embodiment, the strip-shaped images can, for example, simply be placed next to each other in order to compose the image. In an embodiment, the individual strip-shaped images can, for example, also overlap so that, for example, images of higher quality can be generated.

The matrix sensor can, for example, be a CMOS sensor. Such a sensor can be easily adjusted. It is in particular possible that only individual lines be addressed and/or read out. The use of other sensors in which individual lines or areas can be addressed and/or read out is also advantageous. A faster processing is thus possible compared to other sensors where the entire matrix is used for each image.

To obviate the need to adjust an optical device, the arrangement can, for example, comprise at least one aperture for the camera device with a depth of field which extends over an inspection area measured perpendicular to the direction of motion (hereinafter referred to as the measured width) of the plate-shaped object. Since an increase in depth of field is usually achieved through a reduction in the size of the aperture, so that the amount of light is also reduced, the arrangement can therefore, for example, also comprise an illumination device to illuminate the front and/or rear side. The illumination device increases the amount of light so that enough light is still available for a large depth of field.

The arrangement can, for example, comprise a plate-shaped object with a side surface facing the camera device, a front side facing in the direction of motion, and a rear side facing in the opposite direction to the direction of motion, whereby the image processor merges the strip-shaped images recorded in the detection states to form two-dimensional images of the front side, side surface, and rear side.

The camera device can, for example, comprise a read-out module which reads out the areas of the sensor represented as pixel strips.

There may furthermore be an analysis module which examines the front side, rear side and/or side surface of the plate-shaped object for defects.

In an embodiment of the present invention, the arrangement can, for example, comprise a transportation device to transport the plate-shaped objects. The transportation device may be synchronized with the camera device so that images in the first, second or third observation area are always recorded when the relevant parts of the plate-shaped object are located in the observation area.

In addition or as an alternative thereto, a device can, for example, be provided to move the camera. The camera is in this case moved in relation to the object. The plate-shaped objects may be stationary or moving at a speed different from that of the camera device.

The present invention is illustrated in greater detail below using examples on the basis of advantageous embodiments with reference to the drawings. The advantageous further developments and embodiments shown here are independent of each other and can be combined as required, depending on the necessity of the particular application.

FIG. 1 shows a schematic view of plate-shaped objects 5 to be inspected. The plate-shaped objects 5 have the shape of a flat body with a top side 54 designed as a flat side. Adjacent thereto are a front side 51, a side surface 52, and a rear side 53, each of which are designed as narrow sides. The side surface 52 in FIG. 1 was processed. This processing led to defects 6 on the front side 51 and on the rear side 53. Only the side surface 52 is inspected after processing in conventional inspection devices. The defects 6 are not, however, detected in this process. The plate-shaped objects 5 have a height 92 measured along a height direction and a width 82 measured perpendicular thereto along a width direction. An inspection area may comprise the entire width 82 of the plate-shaped object 5 or also a smaller width.

Figure 2:
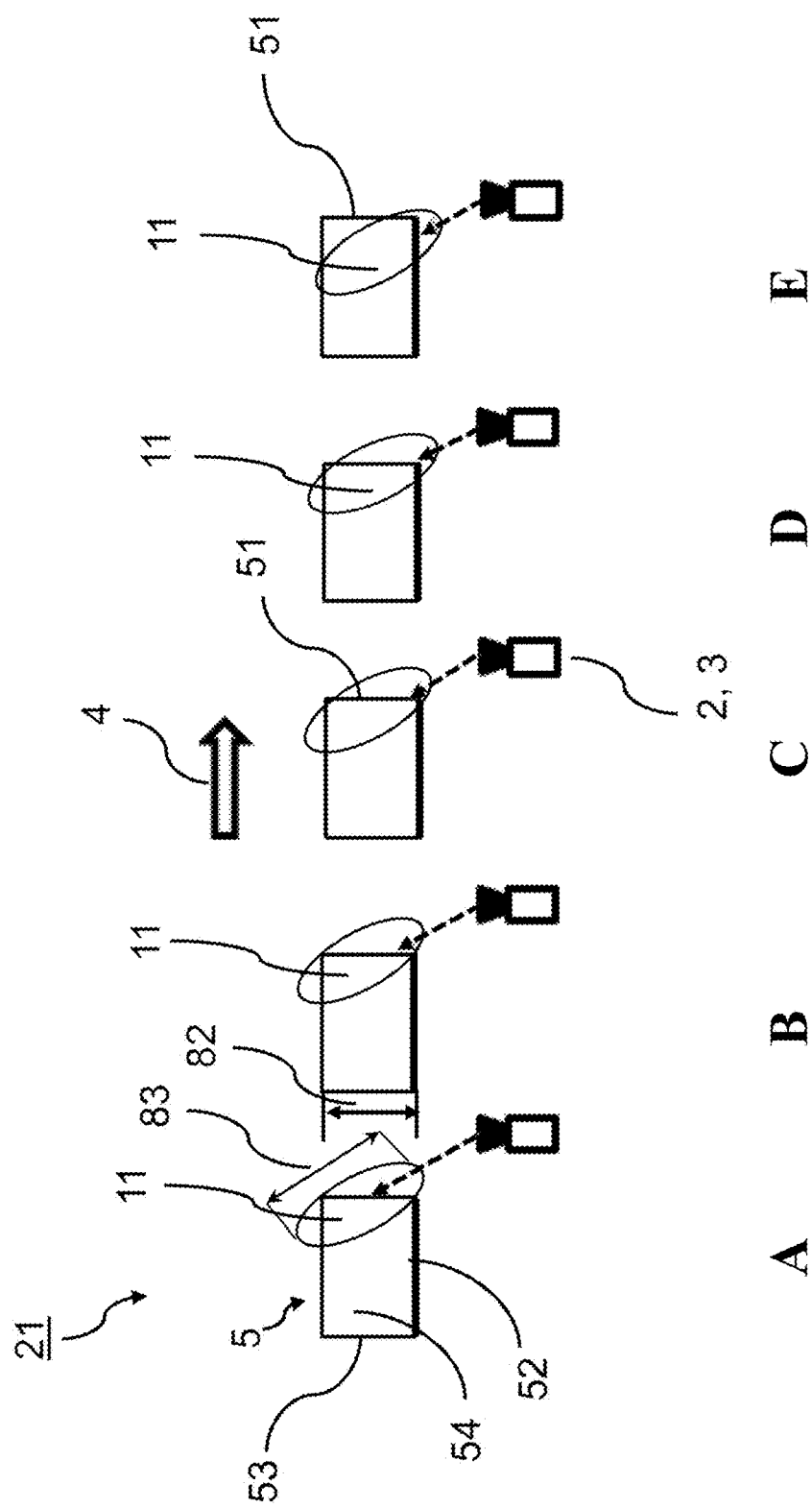
FIG. 2 shows schematic views A-E of the arrangement during different times in a first detection state or measuring interval.
Figure 3:
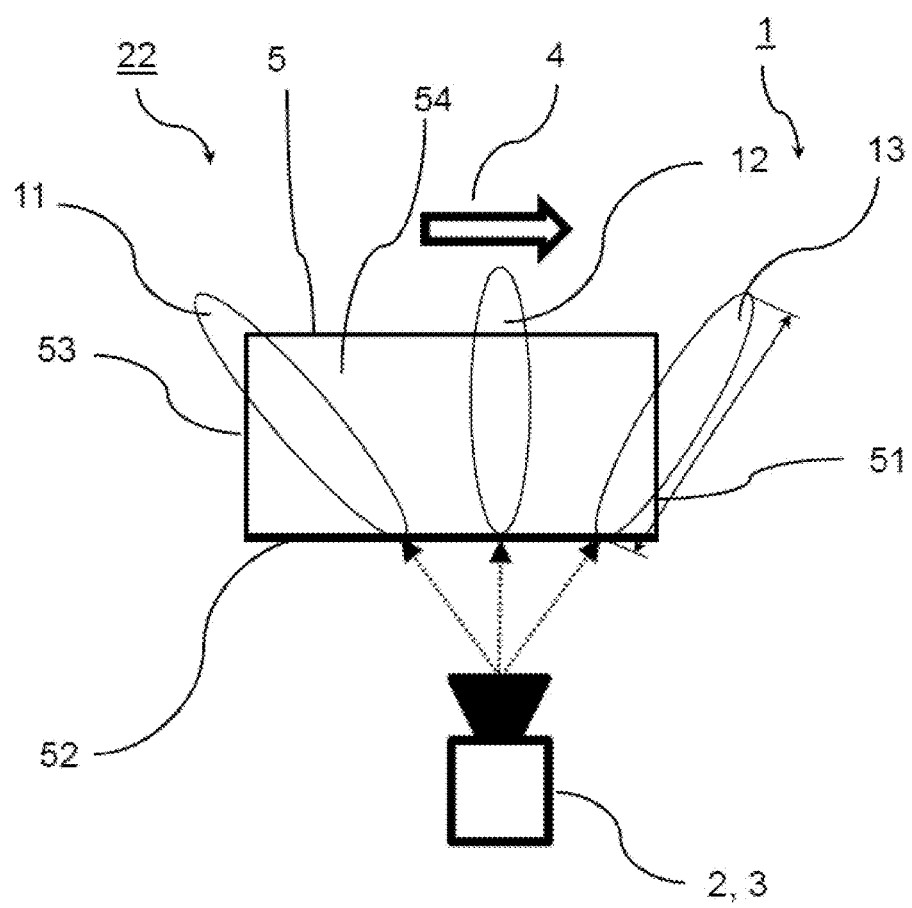
FIG. 3 shows a schematic view during a second detection state or measuring interval.
Figure 4:
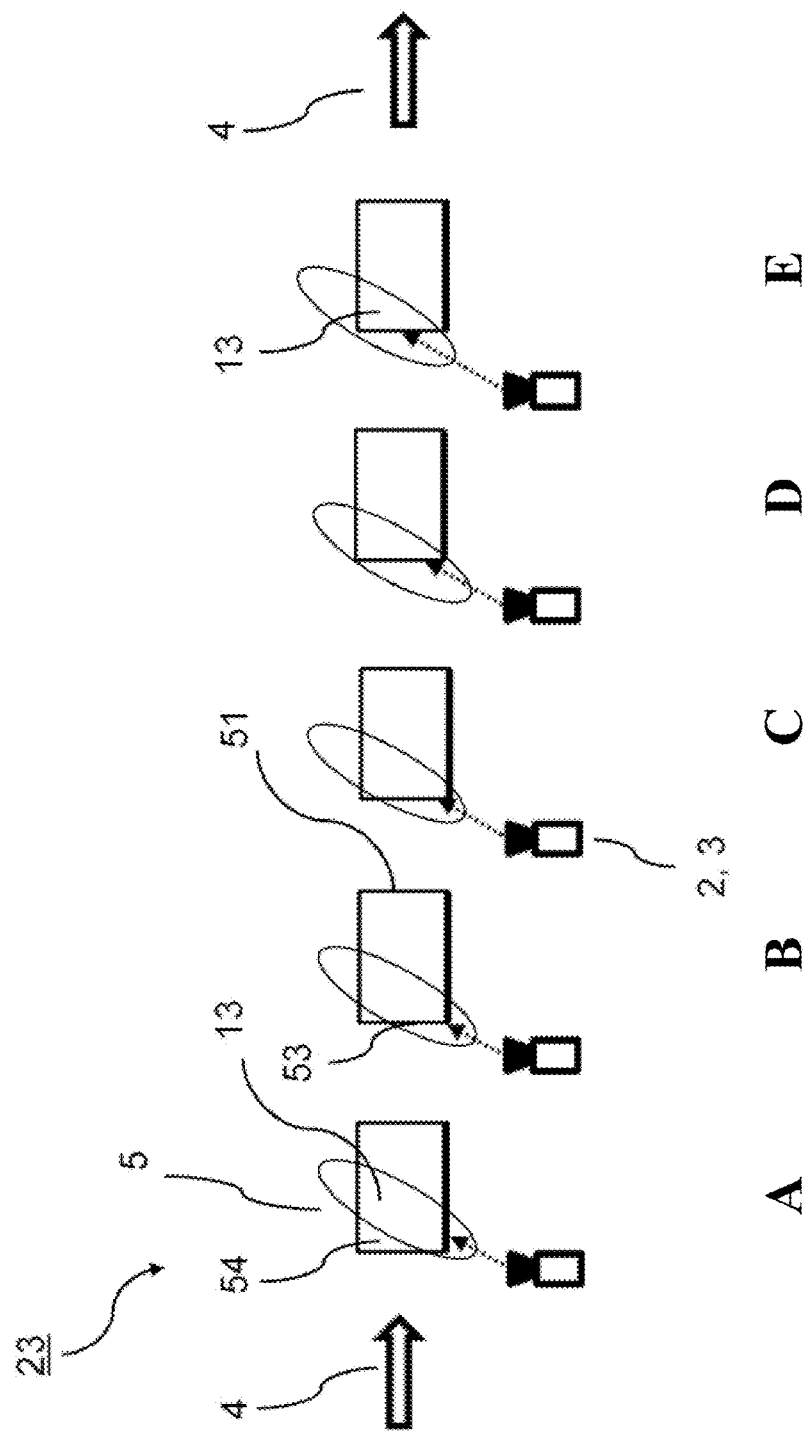
FIG. 4 shows schematic views A-E during different times in a third detection state or measuring interval.

FIGS. 2-4 show three detection states 21, 22, 23 in which the front side 51, the side surface 52, and the rear side 53 are inspected. A plate-shaped object 5 moves along a direction of motion 4 relative to the camera device 2, which in particular comprises a camera 3.

FIG. 2 shows a first detection state 21 at various points in time A-E. During a first detection state 21, strip-shaped images are recorded at the various points in time along a first observation area 11, which runs diagonally opposite to the direction of motion 4. The individual strip-shaped images which were read out by a read-out module of the camera 2 are buffered in a memory, and a two-dimensional image is then generated from the strip-shaped images by merging the strip-shaped images. The two-dimensional image, which in this case corresponds to the front side 51, can then be examined in an analysis module for existing defects 6.

Appropriate measures can be initiated if defects 6 are found; for example, the plate-shaped object 5 may be ejected from the production line for post-processing.

To record the strip-shaped images of the first observation area 11, the latter is imaged on a first image area of a sensor of the camera 3, the first image area being designed as a pixel strip. During the entire first detection state 21, that is, at all points in time shown in FIG. 2 A-E, the first image area remains the same and does not move. A line sensor could therefore also be used instead of a matrix sensor.

In order to obtain a sharp image, the camera 3 has a depth of field 83 which extends over more than the width 82 which is measured along the width direction running perpendicular to the direction of motion 4 and which may correspond to an inspection area of the plate-shaped object 5. As mentioned above, the inspection area may comprise the entire width 82 of the plate-shaped object 5 or also a smaller width. In the shown embodiment, the depth of field 83 corresponds to approximately the length of the first observation area 11. On account of the diagonal course of the first observation area 11, this is projected along the direction of motion 4 in the width direction in order to assess whether the depth of field 83 is sufficient.

A large depth of field 83 can be achieved through an appropriately small-sized aperture. To provide that sufficient light exists in the camera 3 when a small aperture is used, the arrangement can, for example, have an illumination device (not shown in the drawings) which permanently illuminates the plate-shaped object 5 as is required, or which increases a lighting intensity.

In an embodiment of the present invention, the focal length of the camera may also be adjusted during the first detection state 21 in order to obtain a sharp image at each of the points in time. This may be necessary when a suitable depth of field 83 cannot be achieved.

The device may also comprise a transportation device (not shown in the drawings) which moves the plate-shaped objects 5 past the camera 3. The transportation device may in this case in particular be synchronized with the camera 3 so that pictures are only recorded along the observation areas 11, 12, 13 when the plate-shaped objects 5 are in the appropriate positions. The camera 3 may alternatively also move towards the plate-shaped objects 5.

FIG. 3 shows a second detection state 22 in which the side surface 52 is inspected. In this case, the camera 3 measures along a second observation area 12, which in this case is approximately perpendicular to the direction of motion 4. The second observation area 12 may also be at a slight angle to the direction of motion 4 in other embodiments. The second observation area 12 is located between the first observation area 11 and a third observation area 13, which is used for the inspection of the rear side 53. In the second detection state 22 shown in FIG. 3, strip-shaped images are again recorded in a second observation area 12. The individual strip-shaped images recorded in the second detection state 22 are again merged to form a two-dimensional image, which in this case shows the side surface 52. An analysis may here also take place to determine whether there are defects 6 on the side surface 52.

As an alternative to the shown embodiment, a two-dimensional image may be recorded in each of the first and third detection states 21 and 23. If one single two-dimensional image should not be enough, several recorded two-dimensional images may be merged in order to obtain an overall image of the side surface 52.

FIG. 4 shows the arrangement 1 in a third detection state 23 and/or a third observation area 13 in which strip-shaped images of a third observation area 13 are recorded at different points in time A-E and are later merged to form a two-dimensional image. The third observation area 13 runs diagonally in the direction of motion 4.

Figure 5:
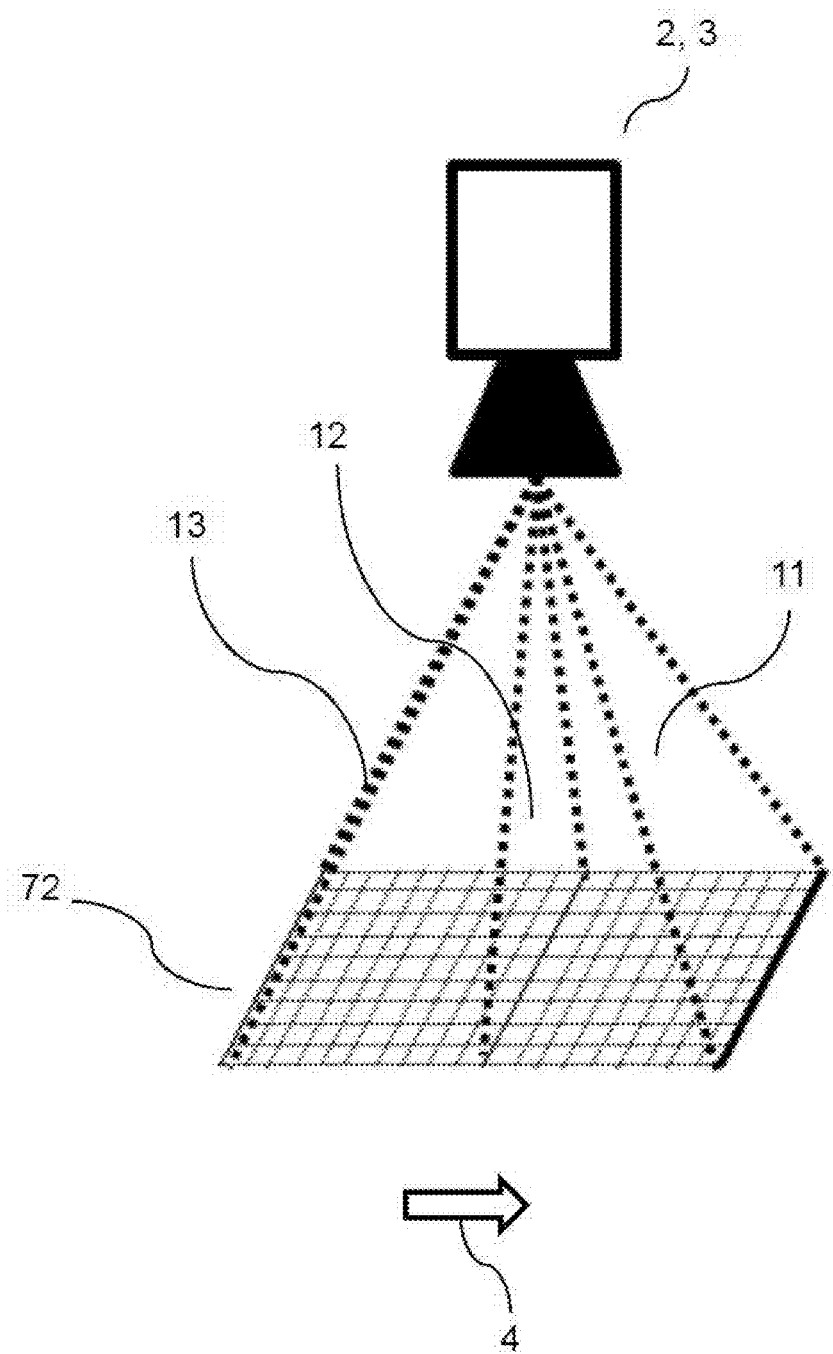
FIG. 5 shows a detailed schematic view of a camera in the arrangement.

FIG. 5 shows a schematic representation of the camera device 2 and the camera 3 with three observation areas 11, 12, 13.

The first observation area 11 is a flat area whose cross-section becomes larger as the distance from the camera 3 increases. It is approximately fan-shaped. The first observation area 11 runs along a first measuring direction, the second observation area 12 extends along a second measuring direction, and the third observation area 13 extends along a third measuring direction. The observation areas 11, 12, 13 and the measuring directions each enclose an angle with the direction of movement 4, whereby the first measuring direction runs opposite to the direction of motion 4 and at an angle thereto, and the third measuring direction runs along the direction of motion 4 and at an angle thereto.

It can also be seen that the camera 3 detects an overall array 72. The camera 3 comprises a matrix sensor with a large number of pixels which are arranged in rows and vertical columns. The first observation area 11 is shown on a first image area, which is designed as a pixel strip. The width of the pixel strip may be one single pixel. In this case, therefore, the pixel strip is formed by a single row of the matrix sensor. The pixel strip in other embodiments may be wider, the pixel strip may, for example, be several pixels wide, in particular 2 to 5 pixels wide. In the image processing shown in FIG. 5, these wider pixel strips can be placed directly next to each other, or overlapping pixel strips may be used to improve the quality.

All three image areas are located on the matrix sensor and are spaced apart. In an alternative embodiment, the three observation areas 11, 12, 13, may also, for example, be imaged on one single image area. This may be achieved by moving parts such as, for example, mirrors.

The matrix sensor is advantageously designed as a CMOS sensor. This type of sensor allows individual lines to be addressed which can increase the recording speed.

As an alternative to the shown embodiment, a line camera can also be used to record the images in the image areas.

Figure 6:
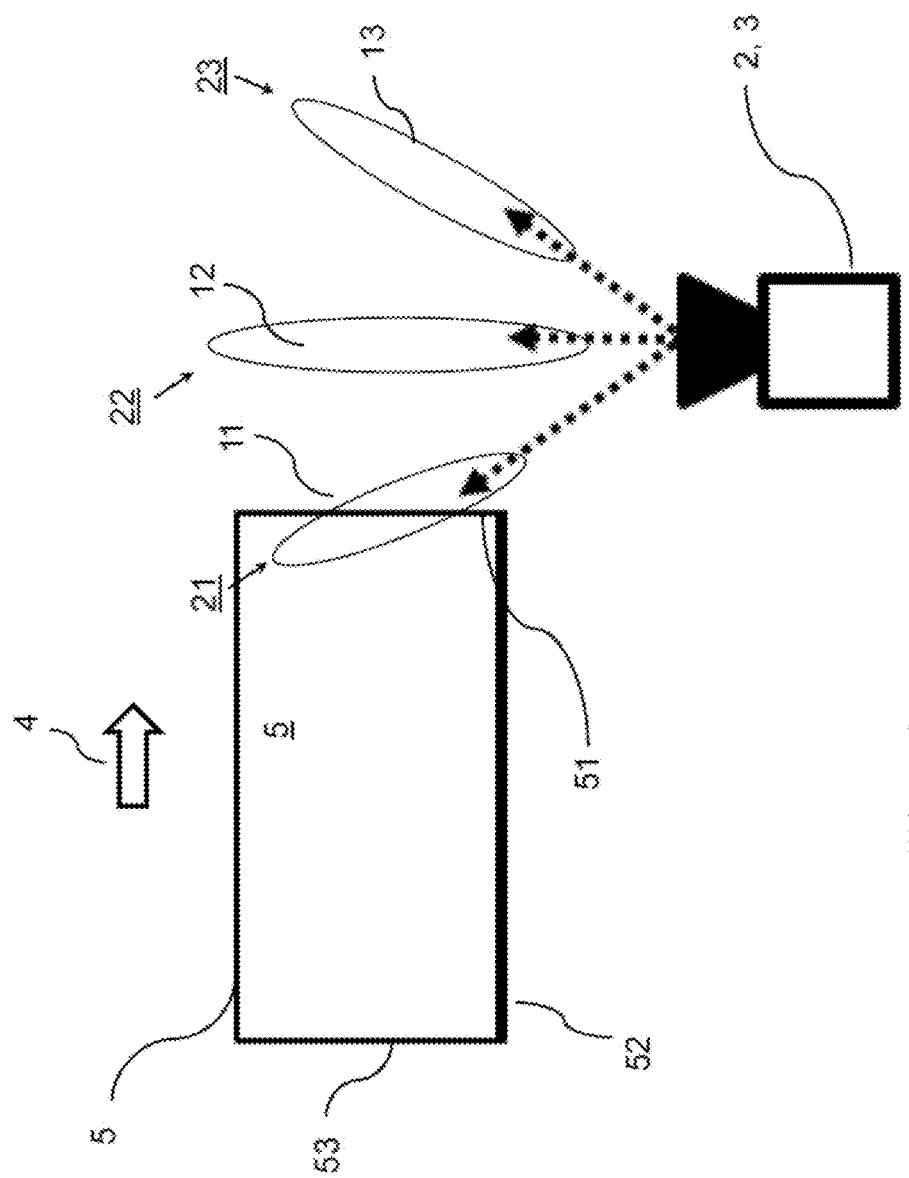
FIG. 6 shows a schematic view of an embodiment of a procedure to which the present invention relates in a first detection state or measuring interval.

FIG. 6 shows a second embodiment which differs slightly from the first embodiment. In this second embodiment, images are recorded in all three observation areas 11, 12, 13 at all points in time. Images that contain no significant information may be discarded in a subsequent step.

The present invention is not limited to embodiments described herein; reference should be had to the appended claims.

What is claimed is:

1. An arrangement for an inspection of plate-shaped objects moving relative to a camera device in a direction of motion through at least two observation areas, the arrangement comprising:

the camera device comprising one single camera which comprises a matrix sensor, and an image processor, wherein, in a first detection state, a first observation area running diagonally opposite to the direction of motion is represented on a first image area of the camera device and is recorded as a strip-shaped image, in a second detection state, a second observation area is represented on a second image area of the camera device and is recorded as a strip-shaped image, the image processor is configured to merge the strip-shaped images recorded in the first detection state and in the second detection state to form two-dimensional images, and all image areas are located on the matrix sensor.

2. The arrangement as recited in claim 1, wherein, in a third detection state, a third observation area running diagonally in the direction of motion is represented on a third image area of the camera device and is recorded as a strip-shaped image, the second observation area is arranged between the first observation area and the third observation area, and the image processor is further configured to merge the strip-shaped images recorded in the first detection state, in the second detection state, and in the third detection state to form two-dimensional images.

3. The arrangement as recited in claim 2, wherein the first image area, the second image area, and the third image area are arranged so as to be spaced apart.

4. The arrangement as recited in claim 2, wherein each of the strip shaped images have a width of one pixel.

5. The arrangement as recited in claim 2, further comprising:

an illumination device, wherein, the camera device comprises at least one aperture having a depth of field which extends at least over the width of the plate-shaped objects when measured perpendicular to the direction of motion, the plate-shaped objects each comprise a front side and a rear side, and the illumination device is configured to illuminate at least one of the front side and the rear side.

6. The arrangement as recited in claim 5, wherein, the plate-shaped objects each further comprise a side surface which faces the camera device, the front side faces in the direction of motion, the rear side faces opposite to the direction of motion, and the image processor is further configured to merge the strip-shaped images recorded in the first detection state, in the second detection state, and in the third detection state to form two-dimensional images of the front side, two-dimensional images of the side surface, and two-dimensional images of the rear side.

7. The arrangement as recited in claim 6, further comprising:

a transportation device configured to transport the plate-shaped objects, the transportation device being synchronized with the camera device.

8. A method of inspecting plate-shaped objects moving relative to a camera device in a direction of motion through at least two observation areas, the process comprising:

recording in a first detection state strip-shaped images along a first observation area running diagonally opposite to the direction of motion;

recording in a second detection state strip-shaped images along a second observation area;

merging the strip-shaped images recorded in the first detection state and in the second detection state to form two-dimensional images, wherein, the second observation area is designed as a pixel strip, the camera device comprises one single camera, the one single camera comprising a matrix sensor, the first observation area is represented on a first image area of the one single camera, the second detection state is represented on a second image area of the camera device, and each of the first image area and the second image area are located on the matrix sensor.

9. The method as recited in claim 8, further comprising:

recording in a third detection state strip-shaped images along a third observation area running diagonally in the direction of motion, and merging the strip-shaped images recorded in the first detection state, in the second detection state, and in the third detection state to form the two-dimensional images, wherein, the second observation area is arranged between the first observation area and the third observation area.

* * * * *